(12) United States Patent
Choi et al.

(10) Patent No.: US 10,016,250 B2
(45) Date of Patent: Jul. 10, 2018

(54) LASER PATTERNING APPARATUS FOR THREE-DIMENSIONAL OBJECT

(71) Applicant: Advanced Technology Inc., Incheon-si (KR)

(72) Inventors: Byoung Chan Choi, Gwangmyeong-si (KR); Doo Baeck An, Incheon-si (KR)

(73) Assignee: Advanced Technology Inc., Incheon-si (KR)

( * ) Notice: Subject to any disclaimer, the term of this patent is extended or adjusted under 35 U.S.C. 154(b) by 0 days.

(21) Appl. No.: 15/640,304

(22) Filed: Jun. 30, 2017

(65) Prior Publication Data

US 2018/0008370 A1    Jan. 11, 2018

(30) Foreign Application Priority Data

Jul. 11, 2016    (KR) .................. 10-2016-0087381

(51) Int. Cl.
*B23K 26/342*     (2014.01)
*A61B 90/00*      (2016.01)
*G01J 1/42*       (2006.01)
*A61F 9/008*      (2006.01)
*B23K 26/03*      (2006.01)
*B23K 26/36*      (2014.01)
*B23K 26/082*     (2014.01)
*B23K 26/0622*    (2014.01)
*G01J 1/04*       (2006.01)

(52) U.S. Cl.
CPC ............ *A61B 90/361* (2016.02); *A61F 9/008* (2013.01); *B23K 26/032* (2013.01); *B23K 26/0624* (2015.10); *B23K 26/082* (2015.10); *B23K 26/36* (2013.01); *G01J 1/4257* (2013.01); *G01J 1/0414* (2013.01)

(58) Field of Classification Search
CPC ..................................... B23K 26/342
USPC ..................................... 219/121.63
See application file for complete search history.

(56) References Cited

U.S. PATENT DOCUMENTS 4,761,534 A * 8/1988 Foulkes ................. B23K 26/04
                                                219/121.63
4,769,523 A * 9/1988 Tanimoto ........... B23K 26/0732
                                                219/121.6
5,284,477 A * 2/1994 Hanna ..................... A61F 9/008
                                                219/121.6

(Continued)

FOREIGN PATENT DOCUMENTS

JP    2011-143615 A      7/2011
KR    10-2012-7002473 A  7/2010
KR    10-1243998 B1      3/2013

*Primary Examiner* — Samuel M Heinrich

(57) ABSTRACT

A laser patterning apparatus for a three-dimensional object includes a laser generator, a beam expander configured to adjust a size of a laser beam generated by the laser generator, a dynamic focusing module configured to adjust a z-axis focus position of the laser beam passing through the beam expander, a scan head configured to adjust x- and y-axis focus position of the laser beam passing through the beam expander, a shape recognizer configured to recognize a shape of a three-dimensional object, and a controller configured to extract x-, y-, and z-axis data of the three-dimensional object and to control the scan head and the dynamic focusing module, in order to pattern the three-dimensional object with the laser beam.

10 Claims, 3 Drawing Sheets

(56) References Cited

U.S. PATENT DOCUMENTS

2005/0150876 A1* 7/2005 Menin ................ B23K 26/0884
              219/121.63
2013/0146569 A1* 6/2013 Woods ................... B23K 26/06
              219/121.64

* cited by examiner

Focus Range in Z-direction

- Field size 120 X 120 : 8mm
- Field size 180 X 180 : 41mm
- Field size 300 X 300 : 202mm

LASER PATTERNING APPARATUS FOR THREE-DIMENSIONAL OBJECT

CROSS-REFERENCE TO RELATED APPLICATION(S)

This application claims priority to Korean Patent Application No. 10-2016-0087381, filed on Jul. 11, 2016, in the Korean Intellectual Property Office, the disclosures of which are incorporated herein by reference in their entirety.

BACKGROUND OF THE INVENTION

Field of the Invention

Exemplary embodiments of the present disclosure relate to a laser patterning apparatus for a three-dimensional object.

Description of the Related Art

Laser machining means an object is processed with a laser beam, and it has also been used for forming a certain pattern on a surface to be processed of an object in recent years. The laser patterning apparatus used for the laser machining is an apparatus that is used to form a predetermined pattern on an object with a laser beam.

However, conventional laser patterning apparatuses three-dimensional curved objects. Moreover, it is difficult to use conventional laser patterning apparatuses because they may not secure high precision and not control errors when patterning objects related to biological transplants such as intraocular lenses.

SUMMARY OF THE INVENTION

Accordingly, the present disclosure is directed to a laser patterning apparatus for a three-dimensional object, which is capable of affecting an array of cells, a movement direction of cells, adhesion of cells, etc. through a micro or nanopattern.

In addition, the present disclosure is to provide a laser patterning apparatus for a three-dimensional object, which is capable of producing a micro to nanoscale pattern with a pulsed laser beam.

In addition, the present disclosure is to provide a laser patterning apparatus for a three-dimensional object, which is capable of uniformly processing a nano to microscale line width using a dynamic focusing module that is able to adjust a focus height of a laser beam.

In addition, the present disclosure is to provide a laser patterning apparatus for a three-dimensional object, which is capable of adjusting movement and adhesion of cells through a micropattern affecting the array of the cells and the movement direction of the cells and a nanopattern affecting the adhesion of the cells.

Furthermore, the present disclosure is to provide a laser patterning apparatus for a three-dimensional object, which is capable of acquiring surface information of a three-dimensional object using any one of an optical coherence tomography (OCT), a laser interferometer, a confocal microscope, and a two-photon microscope.

Additional advantages, objects, and features of the invention will be set forth in part in the description which follows and in part will become apparent to those having ordinary skill in the art upon examination of the following or may be learned from practice of the invention.

In accordance with an aspect of the present disclosure, a laser patterning apparatus for a three-dimensional object includes a laser generator, a beam expander configured to adjust a size of a laser beam generated by the laser generator, a dynamic focusing module configured to adjust a z-axis focus position of the laser beam passing through the beam expander, a scan head configured to adjust x- and y-axis focus position of the laser beam passing through the beam expander, a shape recognizer configured to recognize a shape of a three-dimensional object, and a controller configured to extract x-, y-, and z-axis data of the three-dimensional object and to control the scan head and the dynamic focusing module, in order to pattern the three-dimensional object with the laser beam.

The laser generator may generate one of a nanosecond laser beam, a picosecond laser beam, and a femtosecond laser beam using a pulsed laser beam source.

The beam expander may convert the laser beam into a collimated beam by adjusting the size of the laser beam.

The dynamic focusing module may include a first lens and a second lens, and the dynamic focusing module may adjust convergence and divergence of the laser beam passing through the beam expander by adjusting the first and second lenses, thereby adjusting a z-axis focal point of the laser beam.

The scan head may include a galvanometer including an x-axis scan mirror and a y-axis scan mirror.

The laser patterning apparatus may further include a condenser configured to concentrate the laser beam on the three-dimensional object, and the condenser may include a telecentric F-theta lens or an F-theta lens.

The controller may extract x-, y-, and z-axis surface shape data of the three-dimensional object, and control the dynamic focusing module, adjusting the z-axis focus position of the laser beam, and the scan head, adjusting the x- and y-axis focus position of the laser beam, based on the extracted data, in order to minutely pattern a surface of the three-dimensional object with a micro to nanoscale width and depth.

The shape recognizer may include one of an optical coherence tomography (OCT), a laser interferometer, a confocal microscope, and a two-photon microscope to extract surface shape information including x, y, and z axes of the three-dimensional object.

The three-dimensional object is a biological transplant, and the three-dimensional object may be irradiated with one of a nanosecond laser beam, a picosecond laser beam, and a femtosecond laser beam to form a minute pattern thereon.

The laser patterning apparatus may further include an ultra-precision stage in which the three-dimensional object is controlled to be positioned in an effective processing region and an effective focal length.

It is to be understood that both the foregoing general description and the following detailed description of the present disclosure are exemplary and explanatory and are intended to provide further explanation of the invention as claimed.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF EMBODIMENTS

Exemplary embodiments of the present disclosure will be described below in more detail with reference to the accompanying drawings. The present disclosure may, however, be embodied in different forms and should not be construed as limited to the embodiments set forth herein.

In certain embodiments, detailed descriptions of device constructions or processes well known in the art may be omitted to avoid obscuring appreciation of the disclosure by a person of ordinary skill in the art. In addition, the terms used in the specification are terms defined in consideration of functions of the present disclosure, and these terms may vary with the intention or practice of a user or an operator. Therefore, these terms should be defined based on the entire content disclosed herein.

The present disclosure is defined only by the categories of the claims. These embodiments are provided so that this disclosure will be thorough and complete, and will fully convey the scope of the disclosure to those skilled in the art.

A laser patterning apparatus for a three-dimensional object according to the present disclosure may be used to process a biological transplant, e.g. an intraocular lens, a dental implant, or an orthopedic implant. Meanwhile, the laser patterning apparatus may include a laser generator and a beam adjuster, and may form one or more of a micropattern and a nanopattern, which affect an array and movement direction of cells, in the biological transplant.

Figure 1:
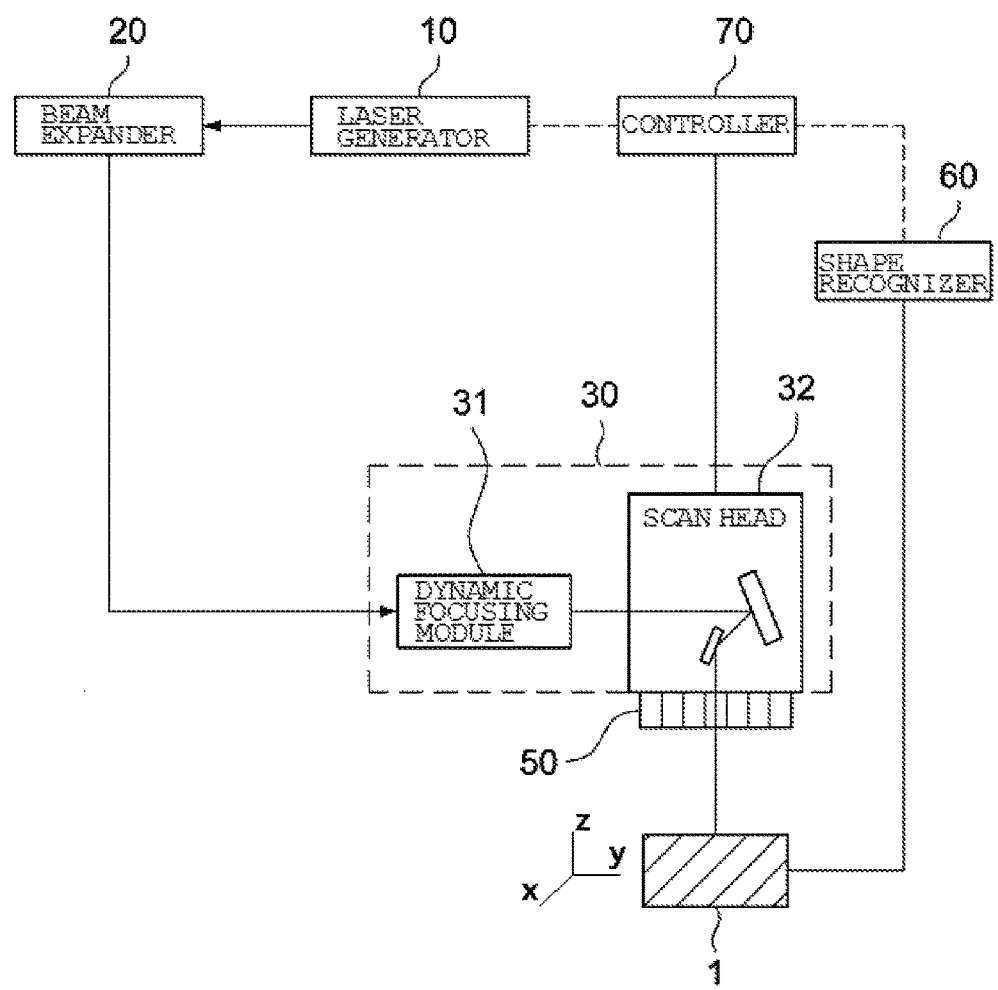
FIG. 1 is a diagram illustrating a laser beam path in a laser patterning apparatus for a three-dimensional object according to an embodiment of the present disclosure.

FIG. 1 is a diagram illustrating a laser beam path in a laser patterning apparatus for a three-dimensional object according to an embodiment of the present disclosure.

Referring to FIG. 1, the laser patterning apparatus for a three-dimensional object according to the embodiment of the present disclosure may include a laser generator 10, a beam expander 20, a beam adjuster 20, a condenser 50, a shape recognizer 60, and a controller 70 in order to minutely pattern a three-dimensional object 1.

The laser generator 10 may generate a laser beam for patterning. Specifically, the laser generator 10 may use a pulsed laser source. Accordingly, the laser generator 10 may generate one of a nanosecond laser beam, a picosecond laser beam, and a femtosecond laser beam. Among them, the femtosecond laser beam may be, for example, a microwave laser beam having a pulse duration of 1 to 1000 femtoseconds. Specifically, the laser generator 10 may generate a pulsed laser beam having a pulse duration in the range of femtoseconds. Here, a pulse repetition rate may be in the two-digit to three-digit kHz range or in the MHz range. The laser patterning apparatus may use a laser beam having any wavelength in the range from infrared to ultraviolet. For example, the wavelength of the laser beam may include an ultraviolet wavelength, a green wavelength, and an infrared wavelength.

The laser patterning apparatus for a three-dimensional object according to the embodiment of the present disclosure may form a pattern having a micro to nanoscale width and depth in the three-dimensional object 1. The laser patterning apparatus may realize various-sized patterns by changing and using a laser wavelength according to the size of the designed pattern. For example, in the case where the three-dimensional object is an intraocular lens from among biological transplants, it is possible to generate a few micro to nanoscale pattern by irradiating the entire surface of the object, having a diameter of 10 mm or more (preferably, a diameter of 12 mm), with a laser beam at a time. That is, the laser patterning apparatus for a three-dimensional object according to the embodiment of the present disclosure may overcome a diffraction limit of the condenser 50 and realize a nanoscale pattern by changing a laser wavelength to have a short ultraviolet wavelength and using the same.

The laser beam generated by the laser generator 10 may be a pulsed femtosecond laser beam, and may pass through the beam expander 20 and the beam adjuster 30.

The beam expander 20 may adjust the size of the laser beam generated by the laser generator 10. Specifically, the beam expander 20 may enlarge or reduce a laser beam. In addition, the beam expander 20 may convert the laser beam into a collimated beam, the dispersion or concentration of which is small. Thus, the laser beam generated by the laser generator 10 may be converted into a collimated beam since it is adjusted in size by enlargement or reduction while passing through the beam expander 20. The size of the laser beam processed by the beam expander 20 may be equal to that of the laser beam incident on the lens in the last stage of the laser patterning apparatus for a three-dimensional object according to the embodiment of the present disclosure. The beam expander 20 may change the diameter of the laser beam generated by the laser generator 10, and output the changed laser beam. The beam expander 20 may be adjusted in a manual or automatic manner.

The laser patterning apparatus may further include a variety of optical elements, such as a polarizer, a half-wave plate, a splitter, a filter, and a shutter, which are arranged therein.

The beam adjuster 30 may adjust the focus height and position of the laser beam emitted to the three-dimensional object. The beam adjuster 30 may include a dynamic focusing module 31 and a scan head 32. The dynamic focusing module 31 of the beam adjuster 30 may adjust the focus height of the laser beam, and the scan head 32 may adjust the focus position of the laser beam along the three-dimensional object.

The dynamic focusing module 31 may adjust the focus position of the laser beam passing through the condenser 50, based on the three-dimensional data of the three-dimensional object. Specifically, the dynamic focusing module 31 may include two lenses. That is, the dynamic focusing module 31 may include a first lens (not shown) and a second lens (not shown). The divergence and convergence of the laser beam passing through the dynamic focusing module 31 may be adjusted by adjusting the distance between the first lens and the second lens, thereby adjusting the focal point of the laser beam passing through the condenser 50.

In other words, the dynamic focusing module 31 may adjust the focus height, i.e. the z-axis focus position, of the laser beam passing through the beam expander 20. The dynamic focusing module 31 may adjust the convergence and divergence of the laser beam passing through the beam expander 20 to adjust the z-axis position of the laser beam, i.e. the focus height of the laser beam.

The dynamic focusing module 31 may adjust the length of the laser beam emitted to the scan head 32 by driving a motor (not shown) that reciprocates horizontally. For example, when the dynamic focusing module 31 moves left by the horizontal reciprocating of the motor, the focal point of the laser beam moves farther from the three-dimensional object 1. Consequently, the laser beam may move upward in the z-direction in FIG. 1 so that the height of the laser beam becomes shorter. On the contrary, when the dynamic focusing module 31 moves right, the laser beam gets closer to the three-dimensional object 1. Consequently, the focal point of the laser beam may move downward in the z-direction in FIG. 1 so that the height of the laser beam gets longer. Accordingly, the focus position of the laser beam incident on the three-dimensional object 1 may be controlled in the z-direction.

The dynamic focusing module 31 may allow the three-dimensional object 1 to be patterned along the height of the three-dimensional surface thereof. For example, since an intraocular lens, one of biological transplants, is curved according to the shape of a cornea, the height (i.e. z-axis position) of the intraocular lens to be patterned with a laser beam may vary depending on the x axis and the y axis. Therefore, it is possible to perform uniform patterning by adjusting the z-axis focus position of the laser beam through the dynamic focusing module 31 so as to correspond to different z-axis positions for respective x- and y-coordinates. In addition, it is possible to perform patterning with a nano to microscale line width. The dynamic focusing module 31 may move an optical system therein or move each of lenses included in the optical system. Thus, it is possible to increase uniformity of a line width on the surface of the three-dimensional object and improve productivity by rapidly controlling the height of the laser beam in real time.

The x- and y-axis focus positions of the laser beam, the z-axis focus positions of which is adjusted by the dynamic focusing module 31, may be adjusted by the scan head 32.

The scan head 32 may adjust the x- and y-axis focus positions of the three-dimensional object 1. The scan head 32 may include an x-axis scan mirror (not shown) and a y-axis scan mirror (not shown), and perform two-dimensional scanning. The x- and y-axis scan mirrors may allow a laser beam to be minutely controlled in the x- and y-directions along the curved surface of the three-dimensional object 1.

The x- and y-axis scan mirrors of the scan head 32 may reflect a laser beam in a direction for patterning to irradiate a desired position of the three-dimensional object 1 with the laser beam. The x- and y-axis scan mirrors may be a pair of galvanometer-type scan mirrors, and the pair of scan mirrors may deflect a laser beam in a direction of one of axes that cross the x-y plane.

Accordingly, the beam adjuster 30 may adjust the focus height and position of the laser beam, as described above. The laser beam may be adjusted in size by enlargement or reduction, while passing through the beam expander 20, to be converted into a collimated beam and be refracted in a controlled direction. The focus position of the laser beam passing through the beam expander 20 may be adjusted so as to correspond to the three-dimensional object 1 in such a manner that the z-axis focus position of the laser beam is adjusted by the dynamic focusing module 31 and the x- and y-coordinates thereof are adjusted by the scan head 32.

The condenser 50 may be disposed beneath the beam adjuster 30 to concentrate the femtosecond laser beam, which passes through the dynamic focusing module 31 and the scan head 32, on the three-dimensional object 1.

The condenser 50 may concentrate a laser beam. The condenser 50 may concentrate the laser beam passing through the beam adjuster 30 to irradiate the three-dimensional object 1 with the laser beam. The condenser 50 may include a telecentric F-theta lens or an F-theta lens. Thus, it is possible to form a micro or nanoscale pattern.

Through these components, it is possible to adjust at least one of various parameters such as the irradiation position and focal length of a laser beam, and the pulse waveform, irradiation time, divergence characteristics, and astigmatism of an output laser beam.

The shape recognizer 60 may recognize the shape of the three-dimensional object 1. As illustrated in FIG. 1, the shape recognizer 60 may be disposed in a space different from the path of the laser beam. The shape recognizer 60 may also be disposed in a path in which a laser beam is transmitted between the dynamic focusing module 31 and the scan head 32. The shape recognizer 60 may recognize the three-dimensional curved surface of the three-dimensional object 1 through an interference phenomenon of light and indicate the same in the figure. It is possible to acquire the shape information of the three-dimensional object 1 through an interferometer using a refractive index, and to transmit the acquired shape information to the controller 70. Specifically, it is difficult to recognize the height and surface of the three-dimensional object 1 because it has a transparent curved shape. Accordingly, it is possible to find a specific point (e.g. a curved apex) of the three-dimensional object 1 by acquiring the three-dimensional surface information of the three-dimensional object 1 through the interferometer using a refractive index, and by matching the acquired information with the figure input to the controller 70. Consequently, it is possible to grasp a position to be patterned by irradiation of a laser beam. It is possible to flexibly perform patterning on various surface structures by the shape recognizer 60.

Moreover, the shape recognizer 60 may include an optical coherence tomography (OCT) to recognize the shape of the three-dimensional object 1. For example, it is possible to scan the transparent curved surface of the three-dimensional object 1 in a three-dimensional manner using a laser beam as an inspection light source to measure coordinates of the three-dimensional surface, and to pattern the surface of the three-dimensional object 1 with a laser beam based on the measured data. Here, the laser beam for laser patterning may be, of course, one of a nanosecond laser beam, a picosecond laser beam, and a femtosecond laser beam. For example, the laser beam may have a wavelength of from greater than 100 nm to 10000 nm and have a pulse repetition rate of 1 Hz to several hundred GHz.

Furthermore, of course, the shape recognizer 60 may include, but not limited to, a confocal microscope or a two-photon microscope to recognize the shape of the three-dimensional object 1. Here, the confocal microscope is a microscope using a confocal principle. The shape recognizer 60 including the confocal microscope may recognize the shape of the three-dimensional object 1 by removing light, which does not coincide with the shape of the three-dimensional object 1, and using only light, which coincides with the focal point of the three-dimensional object 1, from among laser beams. In addition, the shape recognizer 60 may include the two-photon microscope using a two-photon absorption phenomenon to recognize the shape of the three-dimensional object 1.

The controller 70 may receive three-dimensional designed pattern data to extract data of x-, y-, and z-axis focus positions, in order to pattern the curved surface of the three-dimensional object. The scan head 32 may control the two-dimensional data of x- and y-axis focus positions, based on the extracted data. In addition, the dynamic focusing module 32 may control the z-axis focus position data. Thus, the three-dimensional pattern data may be controlled in real time. Therefore, it is possible to minutely pattern the surface of the intraocular lens with a micro to nanoscale width and depth.

Accordingly, the laser patterning apparatus for a three-dimensional object according to the embodiment of the present disclosure may include one of the laser interferometer, the confocal microscope, and the two-photon microscope to extract the three-dimensional surface shape information of the biological transplant, for example the three-dimensional transparent curved surface shape information of the intraocular lens. It is possible to irradiate the surface of the three-dimensional object with a laser beam to pattern the same with a micro to nanoscale width and depth. Of course, the laser beam for laser patterning may be one of a nanosecond laser beam, a picosecond laser beam, and a femtosecond laser beam.

Therefore, it is possible to overcome a pattern centering defect, a pattern cutting defect, a pattern overlapping defect, a product surface flaw, etc. when the surface of the three-dimensional object 1 is patterned with the laser beam.

The laser patterning apparatus for a three-dimensional object according to the embodiment of the present disclosure may further include an ultra-precision stage (not shown). When the three-dimensional object 1 is mounted on the stage for processing, there is a possibility that deformation will occur in which the object is deviated from the effective focal length of an optical system. Accordingly, the three-dimensional object 1 may be controlled to be positioned in the effective processing region and effective focal length of the dynamic focusing module 31 and the scan head 32 according to the combination of a large number of axes in the coordinate system defined by the nano-level ultra-precision stage.

Meanwhile, although not illustrated in the drawings, the three-dimensional object 1 may be an intraocular lens. The intraocular lens may include an optic part in the central region thereof and a haptic part in the peripheral region thereof. The laser patterning apparatus for a three-dimensional object according to the embodiment of the present disclosure may irradiate the haptic part of the intraocular lens with a femtosecond laser beam to minutely pattern the same. By forming a variety of micro or nanoscale patterns in the haptic party, it is possible to achieve an array of cells while having directionality and to achieve movement and adhesion of cells.

Figure 2:
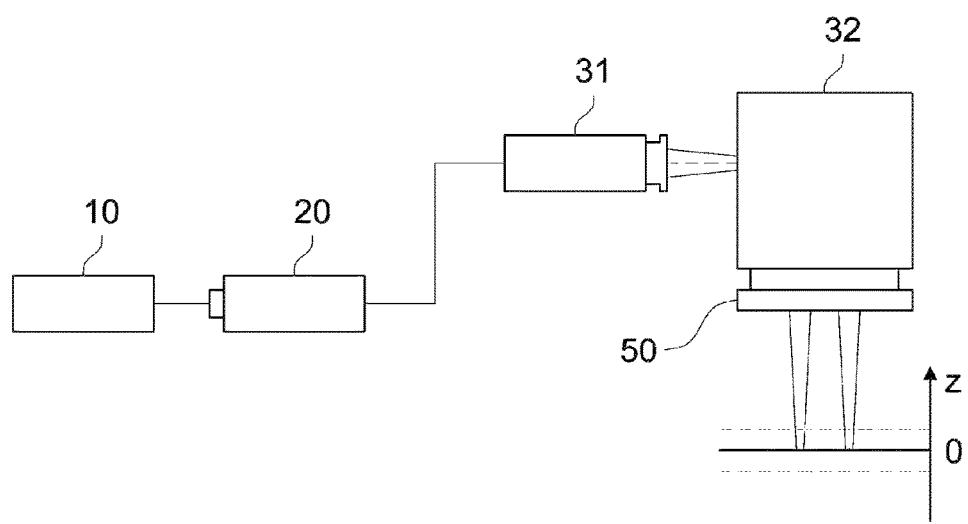
FIG. 2 is a diagram illustrating a beam path for laser patterning of a three-dimensional object according to the embodiment of the present disclosure.
Figure 3:
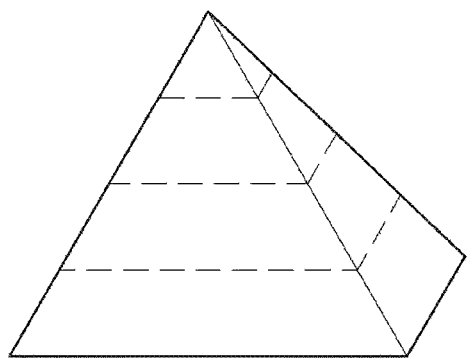
FIG. 3 is a diagram illustrating a beam range for laser patterning according to the embodiment of the present disclosure.

FIGS. 2 and 3 are diagrams illustrating a beam path for laser patterning of the three-dimensional object according to the embodiment of the present disclosure. Referring to FIG. 2, the laser beam generated by the laser generator 10 is transmitted to the beam adjuster 30 through the beam expander 20. The z axis of the laser beam transmitted to the beam adjuster 30 may be adjusted by the dynamic focusing module 31, and the x and y axes of the laser beam may be adjusted by the scan head 32.

Referring to FIG. 3, the three-dimensional object 1 may be irradiated with a laser beam, the x, y, and z axes of which are adjusted by the dynamic focusing module 31 and the scan head 32.

For example, laser beams emitted to the x- and y-axis fields (i.e. imaging surfaces) having different heights of the three-dimensional object 1 may have the same size. The field size in the x- and y-directions is determined according to the specification of a condensing lens of the condenser 50, and thus the focus range in the z-direction may be determined. When the field size in the x- and y-directions is 120 mm×120 mm, the focus range in the z-direction may be 8 mm. In addition, when the field size in the x- and y-directions is 180 mm×180 mm, the focus range in the z-direction may be 41 mm. When the field size in the x- and y-directions is 300 mm×300 mm, the focus range in the z-direction may be 202 mm. That is, the dynamic focusing module 31 may adjust the z axis of the laser beam corresponding to the x- and y-coordinates adjusted by the scan head 32, based on the three-dimensional pattern data of the three-dimensional object 1 input to the controller 70.

As is apparent from the above description, exemplary embodiments of the present disclosure can provide a laser patterning apparatus for a three-dimensional object, which affects an array of cells, a movement direction of cells, adhesion of cells, etc. through a micro or nanopattern.

In addition, it is possible to produce a micro to nanoscale pattern with a pulsed laser beam.

In addition, it is possible to uniformly process a nano to microscale line width using a dynamic focusing module that is able to adjust a focus height of a laser beam.

In addition, it is possible to adjust the movement and adhesion of the cells through the micropattern, which affects the array of the cells and the movement direction of the cells, and the nanopattern which affects the adhesion of the cells.

Furthermore, it is possible to acquire the surface information of a three-dimensional object using any one of an optical coherence tomography (OCT), a laser interferometer, a confocal microscope, and a two-photon microscope.

Although the present disclosure has been described with respect to the illustrative embodiments, it will be apparent to those skilled in the art that various variations and modifications may be made without departing from the spirit and scope of the invention as defined in the following claims.

What is claimed is:

1. A laser patterning apparatus for a three-dimensional object, comprising:
    a laser generator;
    a beam expander configured to adjust a size of a laser beam generated by the laser generator;
    a dynamic focusing module configured to adjust a z-axis focus position of the laser beam passing through the beam expander;
    a scan head configured to adjust x- and y-axis focus position of the laser beam passing through the beam expander;
    a shape recognizer configured to recognize a shape of a three-dimensional object; and
    a controller configured to extract x-, y-, and z-axis data of the three-dimensional object and to control the scan head and the dynamic focusing module, in order to pattern the three-dimensional object with the laser beam.

2. The laser patterning apparatus according to claim 1, wherein the laser generator generates one of a nanosecond laser beam, a picosecond laser beam, and a femtosecond laser beam using a pulsed laser beam source.

3. The laser patterning apparatus according to claim 1, wherein the beam expander converts the laser beam into a collimated beam by adjusting the size of the laser beam.

4. The laser patterning apparatus according to claim 1, wherein:
    the dynamic focusing module comprises a first lens and a second lens; and
    the dynamic focusing module adjusts convergence and divergence of the laser beam passing through the beam expander by adjusting the first and second lenses, thereby adjusting a z-axis focal point of the laser beam.

5. The laser patterning apparatus according to claim 1, wherein the scan head comprises a galvanometer comprising an x-axis scan mirror and a y-axis scan mirror.

6. The laser patterning apparatus according to claim 1, further comprising a condenser configured to concentrate the laser beam on the three-dimensional object,
    wherein the condenser comprises a telecentric F-theta lens or an F-theta lens.

7. The laser patterning apparatus according to claim 1, wherein the controller extracts x-, y-, and z-axis surface shape data of the three-dimensional object, and controls the dynamic focusing module, adjusting the z-axis focus position of the laser beam, and the scan head, adjusting the x- and y-axis focus position of the laser beam, based on the extracted data, in order to minutely pattern a surface of the three-dimensional object with a micro to nanoscale width and depth.

8. The laser patterning apparatus according to claim 1, wherein the shape recognizer comprises one of an optical coherence tomography (OCT), a laser interferometer, a confocal microscope, and a two-photon microscope to extract surface shape information comprising x, y, and z axes of the three-dimensional object.

9. The laser patterning apparatus according to claim 1, wherein:
    the three-dimensional object is a biological transplant; and
    the three-dimensional object is irradiated with one of a nanosecond laser beam, a picosecond laser beam, and a femtosecond laser beam to form a minute pattern thereon.

10. The laser patterning apparatus according to claim 1, further comprising an ultra-precision stage in which the three-dimensional object is controlled to be positioned in an effective processing region and an effective focal length.

\* \* \* \* \*